United States Patent [19]

Wan

[11] Patent Number: 5,329,029
[45] Date of Patent: Jul. 12, 1994

[54] PHOSPHATIDYLALKANOLAMINE DERIVATIVES AND THEIR USE IN GENERATING PHOSPHOLIPID CONJUGATES

[76] Inventor: Barbara Y. Wan, 83 Willow St., Tewksbury, Mass. 01876

[21] Appl. No.: 972,361

[22] Filed: Nov. 5, 1992

[51] Int. Cl.$^5$ ............................................. C07F 9/10
[52] U.S. Cl. ........................................ 554/80; 554/81; 554/82; 558/169; 558/170; 558/174
[58] Field of Search ................... 554/80; 558/174, 170

[56] References Cited

PUBLICATIONS

Hutchinson, F. J. and M. N. Jones FEBS Letters 234(2):493–496 (1988).
Loughrey, H. C. et al., *J. of Immun. Meth.* 132:25–35 (1990).
Afzelius, P. et al., *Biochima et Biophysica Acta.* 979:231–238 (1989).
Heath, T. D., *Methods in Enzymology* 149: 111–119 (1987).
Heath, T. D., and F. J. Martin *Chemistry and Physics of Lipids* 40:347–358 (1986).
Kato, T., *Accounts of Chemical Research* 7:265–271 (1974).

*Primary Examiner*—José G. Dees
*Assistant Examiner*—Dwayne C. Jones
*Attorney, Agent, or Firm*—Beth E. Arnold

[57] ABSTRACT

An efficient, technically straightforward and inexpensive process for generating conjugates of phospholipids with biologically important molecules is described.

3 Claims, No Drawings

PHOSPHATIDYLALKANOLAMINE DERIVATIVES AND THEIR USE IN GENERATING PHOSPHOLIPID CONJUGATES

BACKGROUND OF THE INVENTION

Phospholipids are recognized as one of the most important classes of biological molecules. They are typically composed of a glycerol backbone which is acylated with fatty acids at the $C_1$ and $C_2$ positions and phosphorylated at the remaining terminus. The fatty acids may or may not be identical, and they may vary in degree of unsaturation. In one sub-class of phospholipids, the ether lipids, an ether linkage with an aliphatic chain is formed at the $C_1$ position. Phospholipids are also typically esterified with head groups on the phosphate. Some of the commonly occurring head groups include ethanolamine (phosphatidylethanolamine), choline (phosphatidylcholine), glycerol (phosphatidylglycerol), serine (phosphatidylserine), and inositol (phosphatidylinositol).

Phospholipids have been shown to perform various indispensable cellular functions. They are the major structural components of cell membranes which separate the cytoplasm of the cell from the extracellular medium. Phosphatidylinositol has additionally been shown to be involved in both intracellular and intercellular signal transduction (Hawthorne, J. N., in Phospholipids: Biochemical, pharmaceutical and analytical considerations; I. Hanin and G. Pepeu, Ed.; Plenum Press: New York, 1990; pp 233-240). Dipalmitoyl phosphatidylcholine is an essential component of the pulmonary surfactant which reduces the surface tension in the alveolar membrane (B. Lachmann, ibid., pp 185-196). Platelet activating factor, an ether lipid, plays an important role in inflammation and asthma (Handley, D. A. and R. N. Saunders, Drug Dev. Res. 1986, 7, pp 361-375, and Snyder, F., Med. Res. Rev. 1985, 5, pp 107-140.). Furthermore, phospholipids have found widespread uses in food and cosmetic industries.

Various conjugates of phospholipids with other biologically active molecules have been described in the scientific literature. The phospholipid moiety generally imparts greater hydrophobicity to the conjugate and in some cases, promotes the incorporation of the conjugate onto or the transfer of the conjugate across the cell membrane. It is well known, for example, that muramyl tripeptide-phosphatidylethanolamine (MTP-PE) is active in vivo and is found in various organs 24 hours after injection whereas the parent peptide, muramyl dipeptide, shows activity in vitro and is excreted out of the body 60 minutes after injection (Fogler, W. E., R. Wade, D. E. Brundish, I. J. Fidler, J. Immunol. 1985, 135, pp 1372-1377, and Phillips, N. C., J. Rioux, M.-S. Tsao, Hepatology 1988, 8, pp 1046-1050). These results suggest that the absorption of the peptide is enhanced by conjugation to a lipophilic moiety. Other agents that have been coupled to phospholipids include acyclovir (Welch, C. J., A. Larsson, A. C. Ericson, B. Oberg, R. Datema, J. Chattopadhyaya, Acta Chem. Scand. 1985, B39, pp 47-54), ganglioside $G_{M1}$ (Pacuszka, T., R. M. Bradley, P. H. Fishman, Biochemistry 30, pp 2563-2570), oligosaccharides (Childs, R. A., K. Drickamer, T. Kawasaki, S. Thiel, T. Mizuochi, T. Feizi, Biochem. J. 1989, 262, pp 131-138), serum transferrin (Azelius, P., E. J. F. Demant, G. H. Hansen, P. B. Jensen, Biochim. Biophys. Acta 1989, 979, pp 231-238), biotin, and fluorescent reagents.

Phospholipids are amphiphilic in nature and have a propensity to form micelles and bilayers in an aqueous medium. The bilayers also form closed vesicles called liposomes which have been used to encapsulate molecules of biological interest, including drugs, proteins, vitamins and dyes. Functionalized liposomes are being actively investigated as vehicles for targeted drug delivery. Galactosylated phospholipids, for example, have been incorporated in liposomes and used to deliver the liposomes specifically to asialoglycoprotein receptors of the hepatic system (Haensler, J. and F. Schuber, Glycoconjugate J. 1991, 8, pp 116-124). Immunoliposomes, constructed by covalent conjugation of antibodies to the phospholipid moieties on the liposomal surface, have also shown promise in targeting liposomes to specific cell tissues (Nassander, U. K., P. A. Steerenber, H. Poppe, G. Storm, L. G. Poels, W. H. De Jong, D. J. A. Crommelin, Canc. Res. 1992, 52, pp 646-653, and Pinnaduwage, P. and L. Huang, Biochemistry 1992, 31, pp 2850-2855).

Various methods have been described for derivatizing phospholipids to facilitate their conjugation with other molecules or moieties (for review, see Heath, T. D. and F. J. Martin, Chemistry and Physics of Lipids 1986, 40, pp 347-358). However, each of these methods suffers from various difficulties in practical application. For example, one method comprises glutaraldehyde activation of phosphatidylethanolamine and ultimate conjugation to amines by reductive amination. The problem of dimerization both between the phospholipids and between proteins has made this method less than ideal. An alternative method comprises amide formation between phosphatidylethanolamine and the carboxyl terminus of a peptide or protein. However, this method suffers from low yields and formation of by-products.

In yet another approach, the phospholipid and the protein are first activated and then reacted to form the conjugate. For example, Hutchinson et. al. describe a method in which a phosphatidylethanolamine is activated with N-succinimidyl-S-acetyl-thioacetate (SATA) and treated with a hydroxylamine to yield a phospholipid-thiol derivative. The protein of interest is also activated with maleimide and then treated with the phospholipid derivative to form a stable conjugate via a thioether (Hutchinson et. al., FEBS Lett. 1986, 234, pp 493-6). In a variation of this protocol, the phosphatidylethanolamine is activated with a maleimido moiety and the lysine residue of a protein is activated with a protected thiol (Loughrey, H. C. et. al., J. Immun. Methods 1990, 132, pp 25-35). In practice, protocols employing these approaches are cumbersome to perform and the cost of the derivatizing agent is prohibitively expensive for scales above multigram quantities.

Phospholipid conjugates have also been formed by functionalizing phosphatidylethanolamine using a crosslinking reagent (e.g. dithiobis(succinimidyl propionate)) and reacting this intermediate with a lysine-containing protein so that the succinimidyl moiety is displaced by the amino group of the lysine residue (Afzelius, P., Biochem. Biophys. Acta 1989, 979, pp 231-8). However, crosslinking reagents are not economically feasible for producing phospholipid conjugates, particularly on a large scale. In yet another method, phosphatidylethanolamine may be coupled to glycosylated proteins via the protein carbohydrate chain. For example, glycans can be oxidized with sodium periodate to give reactive aldehydes which can then be coupled to phosphatidylethanolamine via reductive amination with sodium cyanoborohydride (Heath, T. et. al., Biochim. Biophys. Acta 1980, 599:42). This method is limited in its application only to glycoproteins and is often associated with low yields and byproduct formation.

None of the heretofore described methods offer a simple, generally applicable, efficient and economical (i.e. practical) means for generating phospholipid conjugates.

SUMMARY OF THE INVENTION

In general, the invention features a practical process for producing phospholipid conjugates based on reactions which are easily performed. In one aspect, the invention features a novel class of phosphatidylalkanolamines, referred to as N-substituted phosphatidylalkanolamines, which are formed by reacting a phosphatidylalkanolamine with diketene.

In another aspect, the invention features processes for appending a nucleophile to an N-substituted phosphatidylalkanolamine to produce a phospholipid conjugate. For example, in one embodiment, a compound which includes an amino group is reacted with an N-substituted phosphatidylalkanolamine to produce a phospholipid conjugate. Preferably the reaction is carried out under reducing conditions to facilitate the formation of a stable conjugate. In another embodiment, a compound which includes a hydrazino group is reacted with an N-substituted phosphatidylalkanolamine to produce a phospholipid conjugate.

The processes for appending a nucleophile to an N-substituted phosphatidylalkanolamine as described herein provide an efficient means for generating phospholipid conjugates, which can be used for example, for in vivo delivery of proteins, peptides, genes, carbohydrates or drugs. In addition to being technically straightforward, the instant disclosed processes do not require the use of expensive cross-linking agents.

DETAILED DESCRIPTION OF THE INVENTION

The N-substituted phosphatidylalkanolamines of this invention can generally be obtained from corresponding phosphatidylalkanolamines of the general formula:

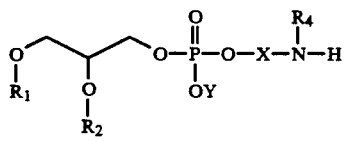

wherein $R_1$, $R_2$ independently represent alkyl, substituted alkyl, alkenyl, substituted alkenyl, alkynyl, substituted alkynyl, aryl, substituted aryl, arylalkyl and substituted arylalkyl; or $C(O)R_3$, wherein $R_3$ represents alkyl, substituted alkyl, alkenyl, substituted alkenyl, alkynyl, substituted alkynyl, aryl, substituted aryl, arylalkyl and substituted arylalkyl $R_4$ represents H, alkyl, aryl X represents alkyl, alkenyl, arylalkyl, substituted alkyl, substituted arylalkyl, substituted alkenyl; and Y represents a cationic moiety including $H^+$, alkali earth metal ions, ammonium ion, and substituted ammonium ions.

For use in the subject invention, a starting phosphatidylalkanolamine (e.g. a 1,2-diacyl-sn-glycero-3-phospho-alkanolamine, 1,2-diacyl-sn-glycero-3-phopho-serine or ether lipid) may be synthetic, semi-synthetic or isolated from natural sources. For example, mixed chain phosphatidylethanolamines can be extracted from bovine brain, sheep brain, bovine liver, porcine liver, soybean, egg yolk or cell extracts from E. coli. Other synthetic phosphatidylethanolamines, like 1,2-distearoyl-sn-glycero-3-phospho-ethanolamine (distearoyl phosphatidylethanolamine) and 1,2-dimyristoyl-sn-glycero-3-phospho-ethanolamine (dimyristoyl phosphatidylethanolamine) can be obtained, for example, from various commercial vendors.

According to one method of the invention, a phosphatidylalkanolamine derivative is produced from a starting phosphatidylalkanolamine upon reaction with diketene. Preferably the reaction is carried out in an organic solvent mixture, (e.g. a mixture of methanol and chloroform or dichloromethane). Solvent mixtures containing primary and secondary amines should be avoided as the amines will compete with the phosphatidylethanolamine for reaction with diketene. Preferably the concentration of the phosphatidylalkanolamine used is in the range of from about 0.01 to 0.1M. A concentration of 0.03M is especially preferred. The reaction should be run at a temperature at which the phosphatidylalkanolamine is completely soluble in organic solvent. For example, temperatures in the range of 20° C. to 50° C. are generally useful, although this range can vary depending on the solvent system and the nature of the phosphatidyl moiety.

An excess of diketene or one of its derivatives of the general formula:

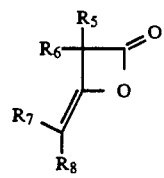

wherein $R_5$, $R_6$, $R_7$, $R_8$ represent H or alkyl, can be added to the phosphatidylalkanolamine solution to initiate the reaction. As used herein, the term "diketene" is used to refer to diketene itself and any of its derivatives. Preferably the ratio of diketene to phosphatidylalkanolamine is in the range of from about 0.9:1 to 40:1, with a ratio of greater than 15:1 being particularly preferred. A low ratio of diketene to phosphatidylalkanolamine or impure diketene may result in partial reactions and low yields.

The reaction mixture can be stirred at the aforementioned temperature until all the phosphatidylalkanolamine has reacted. This typically requires 4 to 48 hours, after which the N-substituted phosphatidylalkanolamine derivative may be isolated using standard methods known to those skilled in the art. For example, the reaction mixture can be concentrated to less than half of its original volume and the product precipitated by acetone. The precipitate, usually a white powder, may be collected either by filtration or centrifugation. More product may be obtained by further evaporation of the mother liquor and precipitation by acetone. Other isolation methods include column chromatography and crystallization. The purified phospholipid derivative may be analyzed for example using nuclear magnetic resonance spectroscopy (NMR), infrared spectroscopy (IR), thin layer chromatography (tlc) or high pressure liquid chromatography (HPLC).

The reactions described above yield N-substituted phosphatidyl-alkanolamines of the general formula:

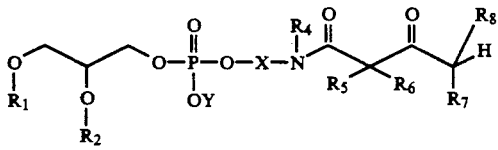

wherein
R$_1$, R$_2$ independently represent alkyl, substituted alkyl, alkenyl, substituted alkenyl, alkynyl, substituted alkynyl, aryl, substituted aryl, arylalkyl and substituted arylalkyl; or C(O)R$_3$,
wherein
R$_3$ represents alkyl, substituted alkyl, alkenyl, substituted alkenyl, alkynyl, substituted alkynyl, aryl, substituted aryl, arylalkyl and substituted arylalkyl
R$_4$ represents H, alkyl, aryl
R$_5$, R$_6$ independently represent H, alkyl
R$_7$, R$_8$ independently represent H, alkyl
X represents alkyl, alkenyl, arylalkyl, substituted alkyl, substituted arylalkyl, substituted alkenyl; and
Y represents a cationic moiety including H$^+$, alkali earth metal ions, ammonium ion, and substituted ammonium ions.

The N-substituted phosphatidylalkanolamines of the subject invention are reactive with nucleophiles, such as amines or hydrazines. Therefore, phospholipid conjugates can be made by reacting N-substituted phosphatidylalkanolamines with nucleophile containing compounds such as amino- (—NH$_2$) or hydrazino- (—NH—NH$_2$) containing compounds.

For example, an N-substituted phosphatidylalkanolamine may be conjugated to peptides, proteins, nucleic acids (e.g. DNA and RNA), carbohydrates or other compounds (e.g. drugs) via a pendant amino group (e.g. via an amino terminus or via a lysine or ornithine residue of a peptide or protein) or via a hydrazino group. Primary and secondary armino groups are preferred, because reactions can proceed without interference due to steric hindrance.

Peptides, proteins or nucleic acids to be conjugated with an N-substituted phosphatidylalkanolamine as described herein may, for example, be synthesized chemically, isolated from natural sources, or obtained via genetic engineering technology. Examples include but are not limited to thyroid stimulating hormone, $\beta$-glucocerebrosidase, cystic fibrosis transmembrane regulator, prolactin, comosain, ananain, $\alpha$-galactosidase, thyrotropin releasing hormone, insulin, peptide portions of these proteins and nucleic acids coding therefore.

In general, conjugation of an N-substituted phosphatidylalkanolamine with an amino compound (e.g. a peptide, protein or nucleic acid containing a pendant amino group) or a hydrazino compound can be accomplished by mixing the two compounds in a suitable medium to form an imine intermediate, which if necessary may be reduced to yield a stable amino linkage.

Preferably, prior to being reacted with an amino or hydrazino compound, an N-substituted phosphatidylalkanolamine is dissolved in an organic solvent. Chlorinated solvents or a mixture of chlorinated solvents and methanol are preferred. An N-substituted phosphatidylalkanolamine may also be dissolved in an aqueous buffer which contains one or more detergents. Preferably the molarity of an N-substituted phosphatidylalkanolamine is in the range of from about 1 mM to 1.0M. However, a molarity in the range of 0.3 to 0.5M is especially preferred. Prior to being reacted with an N-substituted phosphatidylalkanolmine, an amino compound can be dissolved in either an organic or an aqueous medium. Examples of typical organic mediums include chloroform, dichloromethane, methanol, dimethylformamide or dimethylsulfoxide. An example of a typical aqueous medium is a mild buffer solution. However, buffers which contain primary and secondary amines should be avoided as they will compete with the amino group for reaction with the phospholipid.

The ratio of the phospholipid to the amino compound may be 1:1 or any of the two reactants may be in excess. The mixture of N-substituted phosphatidylalkanolamine, amino compound and the reducing agent can be allowed to react at a temperature in the range of about 0° C. to 60° C. for a period of time ranging from about 4 to 60 hrs.

Preferably the pH of the resulting solution is kept in the range of about 3 to 8. However, a pH value in the range of 4 to 6 is especially preferred, as it favors the formation and the subsequent reduction of the imine intermediate.

The imine moiety formed between the phospholipid and the amino compound may be reduced further to give a stable amino linkage. Sodium cyanoborohydride and diborane are preferred reducing agents as they do not interfere with the resulting phosphate ester. The molar ratio of the reducing agent to the imine may vary in accordance with the particular reducing agent used. A preferred ratio of sodium cyanoborohydride to imine is 3 to 1 or higher.

The reductive amination product may be isolated from the mixture for example, by acetone precipitation or, by other standard methods such as silica gel chromatography or crystallization. The new phospholipid-amine conjugate may then be characterized (e.g. using standard tlc, NMR or HPLC methods).

Utility

Phospholipid derivatives made by the method of the subject invention may be compatible with biological membranes. Therefore the N-substituted phosphatidylalkanolamine derivatives can be used for example for in vivo delivery of protein, peptides, nucleic acids, carbohydrates or drugs which are conjugated to the derivative as described herein (Muranishi et. al., *Pharmaceutical Research* 8:649–652 (1991); Nassander et. al., *Cancer Research* 52: 646–653 (1992); Shen et. al., *Advanced Drug Delivery Reviews* 8: 93–113 (1992)). Also the phospholipid conjugates may be useful as fluorescent membrane probes e.g. to study membrane biophysics (Molecular Probes Inc. Catalogue)

The present invention will now be illustrated by the following examples, which are not intended and should not be construed as being limiting in any way.

EXAMPLE 1

Synthesis of 1,2-distearoyl-sn-glycero-3-phospho-(N-acetoacetyl)-ethanolamine (N-acetoacetyl-distearoyl-phosphatidylethanolamine, N-acetoacetyl distearoyl phosphatidylethanolamine, N-acetoacetyl DSPE)

A solution of distearoyl-phosphatidylethanolamine (1.42 g, 1.64 mmol) (Genzyme Corporation, Cambridge, Mass.) in a 3:1 mixture of chloroform/methanol (60 mL total) was warmed to 50° C. until all of the phosphatidylethanolamine dissolved. To the resulting solution was added diketene (5 mL, 65 mmol). The solution was stirred at 40° C. for 6 h. Another batch of diketene (5 mL, 65 mmol) was added. The mixture was then stirred at 40° C. for an additional 16 h. Thin layer chromatography analysis of the reaction mixture on silica coated plate (65:35:5 chloroform/methanol/water, visualized by molybdenum blue reagent) showed that all starting phosphatidylethanolamine ($R_f$ value: 0.49) had reacted and that a new phospholipid derivative ($R_f$ value: 0.54) was formed. The reaction mixture was concentrated under reduced pressure to about one-third of the original volume by rotoevaporation and acetone (about 20 mL) was added to the mixture until a white precipitate formed. The heterogeneous mixture was allowed to stand for about 15 min. The precipitate was collected by centrifugation and washed with cold acetone (5 ml). The collected solid was then dried under high vacuum (560 mg, 36% yield). Additional product was obtained by evaporating the filtrate to about one-sixth of its original volume followed by precipitation with acetone (about 20 mL). The precipitate was collected as described above (650 mg, 42%).

NMR analysis of the product (3:1 CDCl$_3$/MeOH-d4) using a Varian VXR 400 MHz machine showed a downfield shift of the methylene group (—CH$_2$—NH) from 3.2 ppm to 3.4 ppm. The shift is consistent with an amide formed from a primary amine. Furthermore, the presence of a singlet at 2.3 ppm is also indicative of the methyl ketone in the N-acetoacetyl moiety. $^1$H NMR (CDCl$_3$): δ5.25 (br. s, 1 H), 4.37 (dd, J=6, 12 Hz, 1 H), 4.10 (overlapping m and br. s, 5 H), 3.55 (br. s, 2 H), 3.50 (s, 2 H), 2.33 (dd, J=7 Hz, 4 H), 2.30 (s, 3 H), 1.80 (br, s, 4 H), 1.25 (br. s, 56 H), 0.9 (t, J=7 Hz, 6 H).

EXAMPLE 2

Synthesis of 1,2-dimyristoyl-sn-glycero-3-phospho-(N-acetoacetyl-)ethanolamine (N-acetoacetyl dimyristoyl phosphatidylethanolamine, N-acetoacetyl DMPE)

To a solution of dimyristoyl phosphatidylethanolamine (24 mg, 0.03 mmol) (Genzyme Corp., Cambridge, Mass.) in a 3:1 mixture of chloroform/methanol (4 mL) was added an excess of diketene (1 mL). The resulting homogeneous mixture was stirred at room temperature for 19 h. The reaction mixture was concentrated under reduced pressure to less than 1 mL and acetone (about 5 mL) was added to the concentrated reaction mixture. The white precipitate formed was collected by centrifugation as described in example 1 (13 mg, 50%). $^1$H NMR (3:1 CDCl$_3$/MeOH-d4): δ5.17 (br. s, 1 H), 4.32 (br. d, J=11 Hz, 1 H), 4.05 (m, 3 H), 3.93 (m, 2 H), 3.89 (m, 2 H), 3.42 (br. t, J=8.4 Hz, 2 H), 2.25 (t, J=6 Hz, 4 H), 2.21 (s, 3 H), 1.53 (br. s, 4 H), 1.25 (br.s), 0.83 (t, J=6 Hz, 6 H).

EXAMPLE 3

Reductive amination of N-acetoacetyl distearoyl phosphatidylethanolamine with α-N-acetyl lysine methyl ester A solution of N-acetoacetyl distearoyl phosphatidylethanolamine (94 mg, 0.1 mmol), α-N-acetyl lysine ethyl ester (HCl salt, 127 mg, 0.5 mmol) (Sigma Chemical Co.), triethylamine (67 uL, 0.5 mmol), sodium cyanoborohydride (10 mg, 0.16 mmol) was stirred at room temperature for 68 hr. A yellow solution and a small amount of white solid was formed. The solid was removed from the reaction mixture by centrifugation and the resulting solution was evaporated to dryness to give a yellow gum. The yellow gum was triturated with 1:1 methanol/acetone (5 mL) and the white precipitate thus formed was collected by centrifugation (60 mg). The crude product was further purified on a silica gel column equilibrated with 1:1 chloroform/methanol to give a white solid (25 mg, 22% yield). $^1$H NMR (3:1 CDCl$_3$/MeOH-d4) δ5.18 (br.s, 1 H), 4.38 (m, 1 H), 4.35 (dd, J=3, 12 Hz, 1 H), 4.10 (dd, J=5, 12 Hz, 1 H), 4.05 (m, 1 H), 3.9 (t, J=6 Hz, 2 H), 3.68 (s, 3 H), 3.45 (br. d, J=13 Hz, 2 H), 3.20 (m, 1 H), 2.87 (m, 1 H), 2.78 (m, 1 H), 2.42 (br. s, 2 H), 2.25 (overlapping t, J=7 Hz, 4 H), 1.95 (s, 3 H), 1.78 (m, 1 H), 1.62 (m, 3 H), 1.46 (br. s, 4 H), 1.38 (m, 2 H), 1.20 (br. s), 0.8 (overlapping t, J=7 Hz, 6 H). Thin layer chromatography analysis (65:35:5 chloroform/methanol/water): $R_f$ for N-acetoacetyl distearoyl phosphatidyl-ethanolamine 0.69, for product 0.78.

EXAMPLE 4

Reductive Amination of N-acetoacetyl distearoyl phosphatidylethanolamine with Pro-Phe-Gly-Lys To a stirred solution of the tetrapeptide Pro-Phe-Gly-Lys (40 mg, 0.08 mmol) (Sigma Chemical Co.) in methanol (2 mL) was added a solution of N-acetoacetyl distearoyl phosphatidylethanolamine (74 mg, 0.08 mmol) in chloroform (2.5 mL). After stirring at ambient temperature for 30 min, a solution of sodium cyanoborohydride (17 mg, 0.27 mmol) in methanol (1 mL) was added. The resulting solution was allowed to stir at ambient temperature for 16 h, after which the reaction mixture was concentrated under reduced pressure to approximately 1 mL and the product was precipitated by addition of acetone (approximately 5 mL) at ambient temperature. The white precipitate was collected by centrifugation and was washed once with cold acetone (approximately 5 mL). The white precipitate was then redissolved in 1:1 chloroform/methanol and evaporated to dryness. Thin layer chromatography analysis (65:35:5 chloroform/methanol/water)showed disappearance of the N-acetoacetyl distearoyl phosphatidylethanolamine and concomittant formation of a new phospholipid derivative ($R_f$: N-acetoacetyl distearoyl phosphatidylethanolamine: 0.82, major product: 0.89). Reverse phase HPLC analysis of the reaction mixture using a YMC-A-301-3 column showed a major peak which was different from the tetrapeptide and N-acetoacetyl distearoyl phosphatidylethanolamine. HPLC analysis using a Phenomenex Sperisorb 3u Column (normal phase) on a Waters 600 E System equipped with a mass evaporative detector also showed one major peak (retention time: 24.98 min, area percent: 69.7). The HPLC data also confirmed that the new phospholipid derivative, as expected, was more hydrophobic than the tetrapeptide and, more hydrophilic than N-acetoacetyl distearoyl phosphatidylethanolamine.

To further characterize the product, an aliquot of the crude product was passed through a reverse phase column (YMC $C_{18}$ column, 10 mm×250 mm, 40:60:15:0.1 chloroform/methanol/water/trifluoroacetic acid) and the material under the major peak was isolated. The partially purifed product was then subjected to fatty acid and amino acid analyses. Results from these two analyses unequivocally indicated the existence of stearic acid, proline, phenylalanine, glycine and lysine in the same sample, thus confirming that the product isolated contained the amino acid constituents of Pro-Phe-Gly-Lys and the stearic acid residues present in the N-acetoacetyl distearoyl phosphatidylethanolamine reagent. Selected $^1H$ NMR data: δ7.19 (m, 2 H, aromatic H), 7.12 (m, 3 H, aromatic H), 5.13 (m, 1 H, (sn-2)C$\underline{H}$), 4.43 (dd, J=4.4, 8.4 Hz, 1 H, part of (sn-1)C$\underline{H}_2$), 4.07 (dd, J=6.8, 12 Hz, 2 H, (sn-3)C$\underline{H}_2$), 2.21 (t, J=7.5 Hz, 4 H, —O—C(O)—C$\underline{H}_2$—), 0.79 (t, J=7 Hz, 6 H, —O—(O)—C—(CH$_2$)$_{16}$—C$\underline{H}_3$.

EXAMPLE 5

Reductive amination of N-acetoacetyl distearoyl phosphatidylethanolamine with benzyl amine To a stirring solution of N-acetoacetyl distearoyl phosphatidylethanolamine (50 mg. 0.052 mmol) in chloroform (5 mL) was added benzyl amine (35 ul, 0.32 mmol) and sodium cyanoborohydride (10 mg, 0.16 mmol) in methanol (5 mL). The homogeneous solution was stirred at ambient temperature for 18 h. Thin layer chromatography analysis of the reaction mixture (65:35:5 chloroform/methanol/water) showed disappearance of N-acetoacetyl distearoyl phosphatidylethanolamine and appearance of two products ($R_f$ for N-acetoacetyl distearoyl phosphatidylethanolamine: 0.73, for major product: 0.77, for minor product: 0.76). The new phospholipid derivatives were isolated by acetone precipitation and centrifugation as described in example 1. Silica gel column chromatography was used to separate the two products. The minor product was eluted with 3:1 chloroform/methanol (7 mg, 13%) whereas the major product was eluted with 2:1 chloroform/methanol (30 mg, 56%). NMR analysis of the major product confirmed a 1:1 incorporation of benzyl amine into the phospholipid moiety. $^1H$ NMR (3:1 CDCl$_3$/MeOH-d$_4$) δ7.4 (m, 5 H), 5.18 (br. s, 1 H), 4.32 (dd, J=3,12 Hz, 1 H), 4.11 (br. d, J=12 Hz, 1 H), 4.0 (m, 1 H), 3.88 (t, J=6 Hz, 2 H), 3.85 (m, 1 H), 3.41 (br. dd, J=4, 11 Hz, 2 H), 3.29 (m, 1 H), 3.22 (dd, J=4, 10 Hz, 1 H), 3.18 (dd, J=4, 10 Hz, 1 H), 2.50 (dd, J=8, 16 Hz, 1 H), 2.42 (dd, J=4, 16 Hz, 1 H), 2.22 (t, J=7 Hz, 2 H), 2.15 (t, J=7 Hz, 2 H), 1.58 (br.s, 4 H), 1.2 (br.s, 59 H), 0.9 (overlapping t, J=7 Hz, 6 H).

The minor product was dissolved in a 1:1 mixture of chloroform/methanol (1 mL) and further subjected to sodium cyanoborohydride (2 mg) for 16 h at room temperature. Both NMR and tlc indicated that the new product formed from the second reduction was identical to the major product isolated previously, thus suggesting that the minor product was the imine intermediate between the N-acetoacetyl distearoyl phosphatidylethanolamine and benzyl amine.

EXAMPLE 6

Reductive amination of N-acetoacetyl distearoyl phosphatidylethanolamine with Thr-Ser-Lys A solution of the tripeptide, Thr-Ser-Lys (4 mg, 8 umol) (Sigma Chemical Co.), N-acetoacetyl distearoyl phosphatidylethanolamine (11 mg, 12 umol), sodium cyanoborohydride (2 mg, 32 umol) in 1:1 chloroform/methanol (2 mL) was stirred at ambient temperature for 16 h, after which time the reaction mixture was concentrated under reduced pressure to about 0.5 mL, and acetone (about 3 mL) was added. The precipitate thus formed was collected by centrifugation (12 mg, quantitative). Thin layer chromatography on silica: $R_f$ for N-acetoacetyl distearoyl phosphatidylethanolamine 0.73, major product 0.30, minor product 0.45. HPLC analysis using a Phenomenex Sperisorb 3u Column (normal phase) on a Waters 600 E System showed that over 90% of the starting N-acetoacetyl distearoyl phosphatidylethanolamine had reacted to give four new products (retention times: 22,33 min, 22.35%; 23.08 min, 25.82%, 24.43 min, 37.81%, 25.55 min, 10.39%). These new products may represent peptide-phospholipids coupled at the amino terminus of the peptide, at the ε-amino group on the lysine residue, a diphospholipid-peptide coupled at both the amino terminus and the ε-amino group on the lysine, and imine intermediates formed between the N-acetoacetyl distearoyl phosphatidylethanolamine and the peptide.

EXAMPLE 7

Reductive amination of N-acetoacetyl distearoyl phosphatidylethanolamine with Thr-Tyr-Ser To a suspension of the tripepride, Thr-Tyr-Ser (9 mg, 0,024 mmol) (Sigma Chemical Co.) in methanol (2 mL) was added a solution of N-acetoacetyl distearoyl phosphatidylethanolamine (25 mg, 0.026 mmol) in chloroform (2 mL). The mixture was stirred at room temperature for 1 h and sodium cyanoborohydride (10 mg) was added. The mixture was stirred at ambient temperature for 60 h and the solution phase was then separated from the solid phase by decantation. The solution was concentrated under reduced pressure to approximately 1 mL and the desired product mixture was isolated by acetone precipitation (approximately 5 mL). The white precipitate was collected by centrifugation and washed once with cold acetone (28 mg, 82%). Selected $^1H$ NMR data: δ6.99 (dd, J=8 Hz, 2 H, aromatic H on Tyr), 6.66 (br. d, J=8 Hz, 2 H, aromatic H on Tyr), 5.18 (m, 1 H, (sn-2)C$\underline{H}$), 2.23 (br. t, J=7 Hz, 4 H, O—(O)—C—C$\underline{H}_2$—), 1.52 (br. s, 4 H, —O—(O)—C—CH$_2$—C$\underline{H}_2$—), 0.81 (t, J=7 Hz, 6 H, —(O)—C—(CH$_2$)$_{16}$C$\underline{H}_3$).

EXAMPLE 8

Reaction of N-acetoacetyl distearoyl phosphatidylethanolamine with dansyl hydrazide A round-bottom flask was charged with a solution of N-acetoacetyl distearoyl phosphatidylethanolamine (12 mg, 0.013 mmol) in chloroform (0.5 mL) and a solution of dansyl hydrazide (3 mg, 0.011 mmol) (Sigma Chemical Co.) in chloroform (0.9 mL). After stirring at 0° C. for 30 min, N-acetoacetyl distearoyl phosphatidylethanolamine was shown to have completely reacted and a new product, which showed fluorescence activity and was stained by molybdenum blue reagent, was formed.

The reaction mixture was stirred at 0° C. for an additional 60 min and was then evaporated to dryness under reduced pressure. The resultant orange colored solid was purified on a silica gel column. The desired product was eluted from the column with 2:1 chloroform/methanol as a yellowish solid (11 mg, 81%). Thin layer chromatography analysis on silica (65:35:5 chloroform/methanol/water): $R_f$ for N-acetoacetyl distearoyl phosphatidylethanolamine 0.61, for product 0.72 NMR analysis of the product showed the absence of the methyl ketone moiety, and the incorporation of the dansyl moiety as evidenced by the presence of the aromatic protons between 7 and 8 ppm. Selected $^1$H NMR (400 MHz) δ:8.38 (m, 1 H), 8.30 (m, 1 H), 8.10 (m, 1 H), 7.40 (m, 2 H), 7.02 (m, 1 H), 5.05 (m, 1 H), 4.20 (br. d, J=12 Hz, 1 H), 4.0 (m, 2 H) 3.78 (m, 2 H), 3.70 (m, 2 H), 2.70 (s, 3 H), 2.68 (s, 3 H), 2.18 (br. t, J=7 Hz, 4 H), 1.50 (br. s, 4 H), 1.20 (br. s, 56 H), o.78 (t, J=7 Hz, 6 H).

EQUIVALENTS

Those skilled in the art will recognize or be able to ascertain using no more than routine experimentation many equivalents to the specific embodiments of the invention described specifically herein. Such equivalents are intended to be encompassed in the scope of the following claims.

I claim:
1. An N-substituted phosphatidylalkanolamine of the general formula:

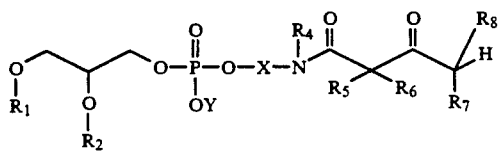

wherein
$R_1$, $R_2$ independently represent alkyl, alkenyl, alkynyl, aryl, arylalkyl, or $C(O)R_3$, wherein $R_3$ represents alkyl, alkenyl, alkynyl, aryl, or arylalkyl;
$R_4$ represents H, alkyl or aryl;
$R_5$, $R_6$ independently represent H, or alkyl;
$R_7$, $R_8$ independently represent H, or alkyl;
X represents alkyl, alkenyl or arylalkyl; and
Y represents a cationic moiety including H+, alkali earth metal ions or ammonium ions.

2. An N-substituted phosphatidylalkanolamine as in claim 1 selected from the group consisting of 1,2-distearoyl-sn-glycero-3-phospho- (N-acetoacetyl)-ethanolamine and 1,2-dimyristoyl-sn-glycero-3-phospho-(N-acetoacetyl) ethanolamine.

3. An N-substituted phosphatidylalkanolamine of the general formula:

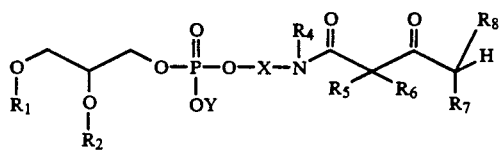

wherein
$R_1$ and $R_2$ independently comprise a fatty acid residue,
$R_4$ comprises H, alkyl or aryl
$R_5$, $R_6$, $R_7$ and $R_8$ independently comprise H or an alkyl,
X comprises alkyl, alkenyl or arylalkyl; and
Y comprises H+.

* * * * *